(12) United States Patent
Lee et al.

(10) Patent No.: US 9,834,620 B2
(45) Date of Patent: Dec. 5, 2017

(54) MODIFIED CONJUGATED DIENE-BASED POLYMER, PREPARATION METHOD THEREFOR, AND RUBBER COMPOSITION CONTAINING SAME

(71) Applicant: LG Chem, Ltd., Seoul (KR)

(72) Inventors: He-Seung Lee, Daejeon (KR); No-Ma Kim, Daejeon (KR); Hae-Sung Sohn, Daejeon (KR)

(73) Assignee: LG Chem, Ltd. (KR)

( * ) Notice: Subject to any disclaimer, the term of this patent is extended or adjusted under 35 U.S.C. 154(b) by 0 days.

(21) Appl. No.: 15/121,848

(22) PCT Filed: Dec. 11, 2015

(86) PCT No.: PCT/KR2015/013630
§ 371 (c)(1),
(2) Date: Aug. 26, 2016

(87) PCT Pub. No.: WO2016/093671
PCT Pub. Date: Jun. 16, 2016

(65) Prior Publication Data
US 2017/0015761 A1    Jan. 19, 2017

(30) Foreign Application Priority Data

Dec. 11, 2014   (KR) .................. 10-2014-0178304
Dec. 10, 2015   (KR) .................. 10-2015-0175951

(51) Int. Cl.
| | |
|---|---|
| *C08C 19/25* | (2006.01) |
| *C08C 19/22* | (2006.01) |
| *C07D 241/00* | (2006.01) |
| *C07F 7/18* | (2006.01) |
| *B60C 1/00* | (2006.01) |
| *C08F 36/04* | (2006.01) |
| *C08C 19/26* | (2006.01) |
| *C08L 15/00* | (2006.01) |
| *C08C 19/44* | (2006.01) |
| *C08F 236/06* | (2006.01) |
| *C08K 3/04* | (2006.01) |
| *C08K 3/36* | (2006.01) |

(52) U.S. Cl.
CPC ............. *C08C 19/25* (2013.01); *B60C 1/00* (2013.01); *B60C 1/0016* (2013.01); *C07D 241/00* (2013.01); *C07F 7/1816* (2013.01); *C08C 19/22* (2013.01); *C08C 19/26* (2013.01); *C08C 19/44* (2013.01); *C08F 36/04* (2013.01); *C08F 236/06* (2013.01); *C08K 3/04* (2013.01); *C08K 3/36* (2013.01); *C08L 15/00* (2013.01); *C08F 2500/04* (2013.01); *C08F 2500/17* (2013.01); *C08F 2800/20* (2013.01)

(58) Field of Classification Search
CPC ................................ C08C 19/22; C08C 19/25
USPC .............................. 525/342, 374, 375, 382
See application file for complete search history.

(56) References Cited

U.S. PATENT DOCUMENTS

| | | |
|---|---|---|
| 3,779,703 A | 12/1973 | Tesoro |
| 2009/0163668 A1 | 6/2009 | Yamada et al. |
| 2009/0203843 A1 | 8/2009 | Fukuoka et al. |
| 2012/0270997 A1 | 10/2012 | Tanaka et al. |
| 2012/0277369 A1 | 11/2012 | Yoshida et al. |
| 2013/0172481 A1 | 7/2013 | Okada et al. |
| 2014/0243447 A1 | 8/2014 | Cho et al. |
| 2014/0357784 A1 | 12/2014 | Morita et al. |

FOREIGN PATENT DOCUMENTS

| | | |
|---|---|---|
| EP | 2338919 A1 | 6/2011 |
| EP | 2752433 A1 | 7/2014 |
| JP | 2013139491 A | 7/2013 |
| KR | 101310868 B1 | 10/2013 |
| WO | 2007034785 A1 | 3/2007 |
| WO | 2007114203 A1 | 10/2007 |
| WO | 2008013090 A1 | 1/2008 |
| WO | 2011040312 A1 | 4/2011 |

OTHER PUBLICATIONS

International Search Report from PCT/KR2015/013630, dated Apr. 1, 2016.
Extended European Search Report for Application No. 15868382.1 dated Jan. 20, 2017.

*Primary Examiner* — Marc Zimmer
(74) *Attorney, Agent, or Firm* — Lerner, David, Littenberg, Krumholz & Mentlik, LLP

(57) ABSTRACT

Disclosed are a modified conjugated diene-based polymer represented by specific Chemical Formula, a method of preparing the same, and a rubber composition including the same.

19 Claims, No Drawings

MODIFIED CONJUGATED DIENE-BASED POLYMER, PREPARATION METHOD THEREFOR, AND RUBBER COMPOSITION CONTAINING SAME

CROSS-REFERENCE TO RELATED APPLICATION

This application is a national phase entry under 35 U.S.C. §371 of International Application No. PCT/KR2015/013630, filed Dec. 11, 2015, which claims priority to Korean Patent Application No. 10-2014-0178304, filed Dec. 11, 2014 and Korean Patent Application No. 10-2015-0175951, filed Dec. 10, 2015, the disclosures of which are incorporated herein by reference.

TECHNICAL FIELD

The present invention relates to a modified conjugated diene-based polymer, a method of preparing the same, and a rubber composition including the same and, more particularly, to a modified conjugated diene-based polymer having high tensile strength, wear resistance, and wet skid resistance, as well as improved heat build-up when mixed with silica as a reinforcing agent, a method of preparing the same, and a rubber composition including the same.

BACKGROUND ART

Recently, in the vehicle industry, there is a continuous demand for vehicles to exhibit increased durability, stability and fuel economy, and much effort is directed to satisfying the demand.

In particular, many attempts have been made to enhance the properties of rubber, as a material for vehicle tires, especially tire treads, which are in contact with roads. The rubber composition for a vehicle tire contains a conjugated diene-based polymer, such as polybutadiene or butadiene-styrene copolymer.

Thorough research is currently ongoing into the addition of various reinforcing agents to conjugated diene-based rubber compositions to increase the performance of vehicle tires. Specifically, as vehicles are required to exhibit stability, durability and fuel economy, rubber compositions having excellent wet skid resistance and mechanical strength, as well as improved heat build-up, are being developed as material for vehicle tires, especially tire treads, which are in contact with roads.

DISCLOSURE

Technical Problem

Therefore, the present invention has been made keeping in mind the above problems encountered in the related art, and an object of the present invention is to provide a modified conjugated diene-based polymer having high tensile strength, wear resistance, and wet skid resistance, as well as improved heat build-up when mixed with silica as a reinforcing agent, a method of preparing the same, and a rubber composition including the same.

Technical Solution

In order to accomplish the above object, the present invention provides a modified conjugated diene-based polymer represented by Chemical Formula 2 below:

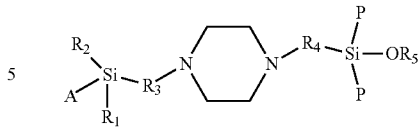

[Chemical Formula 2]

in Chemical Formula 2, $R_1$ and $R_2$, which are identical to or different from each other, are each a C1-C10 alkyl group, $R_3$ and $R_4$, which are identical to or different from each other, are each a C1-C10 alkylene group, $R_5$ is a C1-C10 alkyl group, and A is P or $OR_6$, wherein P is a conjugated diene-based polymer chain and $R_6$ is a C1-C10 alkyl group.

In addition, the present invention provides a method of preparing a modified conjugated diene-based polymer, comprising: a) polymerizing a conjugated diene monomer, or a conjugated diene monomer and an aromatic vinyl monomer, using a hydrocarbon solvent in the presence of an organoalkali metal compound, thus forming an active conjugated diene-based polymer having an alkali metal end; and b) coupling or reacting the active conjugated diene-based polymer having the alkali metal end with the compound represented by Chemical Formula 1 below, yielding the modified conjugated diene-based polymer represented by Chemical Formula 2 below:

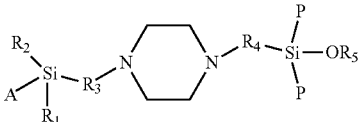

[Chemical Formula 1]

in Chemical Formula 1, $R_1$ and $R_2$, which are identical to or different from each other, are each a C1-C10 alkyl group, $R_3$ and $R_4$, which are identical to or different from each other, are each a C1-C10 alkylene group, and $R_5$ and $R_6$, which are identical to or different from each other, are each a C1-C10 alkyl group; and

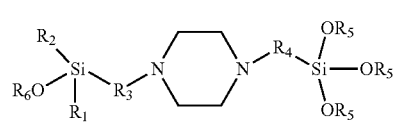

[Chemical Formula 2]

in Chemical Formula 2, $R_1$ and $R_2$, which are identical to or different from each other, are each a C1-C10 alkyl group, $R_3$ and $R_4$, which are identical to or different from each other, are each a C1-C10 alkylene group, $R_5$ is a C1-C10 alkyl group, and A is P or $OR_6$, wherein P is a conjugated diene-based polymer chain and $R_6$ is a C1-C10 alkyl group.

In addition, the present invention provides a modified conjugated diene-based polymer rubber composition comprising 100 parts by weight of the modified conjugated diene-based polymer and 0.1 to 200 parts by weight of an inorganic filler.

In addition, the present invention provides a modifier, which is a compound represented by Chemical Formula 1 below:

[Chemical Formula 1]

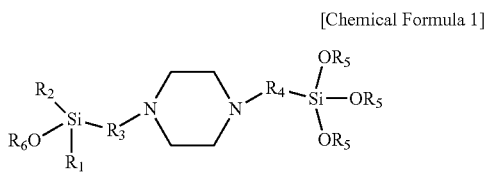

in Chemical Formula 1, $R_1$ and $R_2$, which are identical to or different from each other, are each a C1-C10 alkyl group, $R_3$ and $R_4$, which are identical to or different from each other, are each a C1-C10 alkylene group, and $R_5$ and $R_6$, which are identical to or different from each other, are each a C1-C10 alkyl group.

In addition, the present invention provides a tire or tire tread comprising the modified conjugated diene-based polymer rubber composition.

Advantageous Effects

According to the present invention, a modified conjugated diene-based polymer, which exhibits high tensile strength, wear resistance, and wet skid resistance, as well as improved heat build-up when mixed with silica as a reinforcing agent, can be prepared, and can be utilized to produce a rubber composition for a tire.

BEST MODE

Hereinafter, a detailed description will be given of the present invention. Prior thereto, the terms or words used in the description and the claims of the present invention are not to be construed limitedly as having typical or dictionary meanings and should be interpreted as having the meanings and concepts of the invention in keeping with the scope of the invention based on the principle that the inventors can appropriately define the terms in order to describe the invention in the best way.

Therefore, the examples described in the present specification are merely preferred embodiments of the present invention, and do not represent all of the technical ideas of the present invention, and thus, it is to be understood that a variety of equivalents and modifications able to substitute therefor may be provided at the point of time at which the present invention is filed.

An aspect of the present invention addresses a modified conjugated diene-based polymer represented by Chemical Formula 2 below:

[Chemical Formula 2]

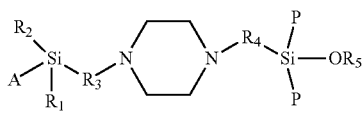

in Chemical Formula 2, $R_1$ and $R_2$, which are identical to or different from each other, are each a C1-C10 alkyl group, $R_3$ and $R_4$, which are identical to or different from each other, are each a C1-C10 alkylene group, $R_5$ is a C1-C10 alkyl group, and A is P or $OR_6$, wherein P is a conjugated diene-based polymer chain and $R_6$ is a C1-C10 alkyl group.

Chemical Formula 2 may be represented by, for example, Chemical Formula 3 or 4 below:

[Chemical Formula 3]

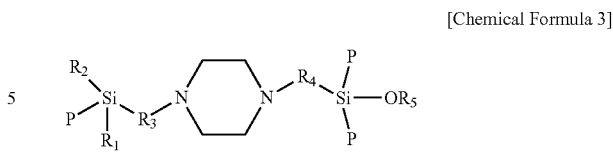

in Chemical Formula 3, $R_1$ and $R_2$, which are identical to or different from each other, are each a C1-C10 alkyl group, $R_3$ and $R_4$, which are identical to or different from each other, are each a C1-C10 alkylene group, $R_5$ is a C1-C10 alkyl group, and P is a conjugated diene-based polymer chain; and

[Chemical Formula 4]

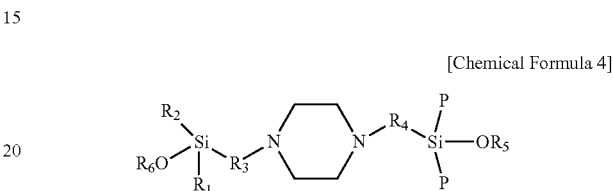

in Chemical Formula 4, $R_1$ and $R_2$, which are identical to or different from each other, are each a C1-C10 alkyl group, $R_3$ and $R_4$, which are identical to or different from each other, are each a C1-C10 alkylene group, and $R_5$ and $R_6$, which are identical to or different from each other, are each a C1-C10 alkyl group.

The modified conjugated diene-based polymer represented by Chemical Formula 3 is configured such that three portions are coupled, and the modified conjugated diene-based polymer represented by Chemical Formula 4 is configured such that two portions are coupled. In this case in particular, the affinity for silica may be increased owing to the unreacted alkoxy structures.

The modified conjugated diene-based polymer may have a number average molecular weight (Mn) of 1,000 to 2,000,000 g/mol, preferably 10,000 to 1,000,000 g/mol, and more preferably 100,000 to 1,000,000 g/mol. When the number average molecular weight of the modified conjugated diene-based polymer falls in the above range, a modification reaction may efficiently occur, and desired properties may be obtained.

The modified conjugated diene-based polymer may have a polydispersity index (Mw/Mn) of 1 to 10, preferably 1 to 5, and more preferably 1 to 4. When the polydispersity index of the modified conjugated diene-based polymer falls in the above range, mixing with inorganic particles may be efficiently carried out, thus ensuring desired properties and remarkably increasing processability.

The modified conjugated diene-based polymer may have a vinyl content of 10 wt % or more, preferably 15 wt % or more, and more preferably 20 to 70 wt %.

The vinyl content refers to the amount of a monomer having a vinyl group, or the amount of 1,2-added conjugated diene monomer rather than the amount of 1,4-added conjugated diene monomer, based on 100 wt % of the conjugated diene monomer.

Given the above vinyl content range, the glass transition temperature of the polymer may be elevated. Thus, when such a polymer is applied to tires, the properties required of tires, such as running resistance and wet grip, may be satisfied, and superior fuel economy may result.

The conjugated diene-based polymer chain may be derived from a homopolymer of a conjugated diene monomer or a copolymer of a conjugated diene monomer and a vinyl aromatic monomer.

Specifically, the conjugated diene-based polymer chain may be formed in a way in which a conjugated diene monomer, or a conjugated diene monomer and a vinyl aromatic monomer, may be polymerized in a batch manner or a continuous manner using a hydrocarbon solvent in the presence of an organo-alkali metal compound, thus obtaining a homopolymer or copolymer having an alkali metal end, which is then reacted with a silyl group substituted with at least one alkoxy group.

As such, the conjugated diene-based polymer chain may be a polymer chain comprising the aromatic vinyl monomer in an amount of 0.0001 to 50 wt %, 10 to 40 wt %, or 20 to 40 wt %, based on 100 wt % in total of the conjugated diene monomer, or the conjugated diene monomer and the vinyl aromatic monomer.

The polymer chain comprising the conjugated diene monomer and the vinyl aromatic monomer may be, for example, a random polymer chain.

The conjugated diene monomer may include at least one selected from the group consisting of 1,3-butadiene, 2,3-dimethyl-1,3-butadiene, piperylene, 3-butyl-1,3-octadiene, isoprene, and 2-phenyl-1,3-butadiene.

The vinyl aromatic monomer may include at least one selected from the group consisting of styrene, α-methylstyrene, 3-methylstyrene, 4-methylstyrene, 4-propylstyrene, 1-vinylnaphthalene, 4-cyclohexylstyrene, 4-(p-methylphenyl)styrene, and 1-vinyl-5-hexylnaphthalene. Particularly useful is styrene or α-methylstyrene.

The modified conjugated diene-based polymer may have a Mooney viscosity of 40 or more, preferably from 40 to 100, and more preferably from 45 to 90. Given the above Mooney viscosity range, a modified conjugated diene-based polymer having improved heat build-up and high processability, compatibility, tensile strength, wear resistance, fuel economy, and wet skid resistance may be prepared.

Another aspect of the present invention addresses a method of preparing a modified conjugated diene-based polymer, comprising: a) polymerizing a conjugated diene monomer, or a conjugated diene monomer and an aromatic vinyl monomer, using a hydrocarbon solvent in the presence of an organo-alkali metal compound, thus forming an active conjugated diene-based polymer having an alkali metal end; and b) coupling or reacting the active conjugated diene-based polymer having the alkali metal end with the compound represented by Chemical Formula 1 below, yielding the modified conjugated diene-based polymer represented by Chemical Formula 2 below:

[Chemical Formula 1]

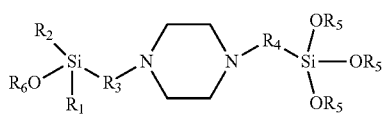

in Chemical Formula 1, $R_1$ and $R_2$, which are identical to or different from each other, are each a C1-C10 alkyl group, $R_3$ and $R_4$, which are identical to or different from each other, are each a C1-C10 alkylene group, and $R_5$ and $R_6$, which are identical to or different from each other, are each a C1-C10 alkyl group; and

[Chemical Formula 2]

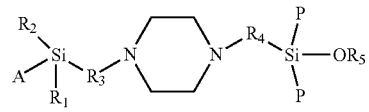

in Chemical Formula 2, $R_1$ and $R_2$, which are identical to or different from each other, are each a C1-C10 alkyl group, $R_3$ and $R_4$, which are identical to or different from each other, are each a C1-C10 alkylene group, $R_5$ is a C1-C10 alkyl group, and A is P or $OR_6$, wherein P is a conjugated diene-based polymer chain and $R_6$ is a C1-C10 alkyl group.

Chemical Formula 2 may be represented by, for example, Chemical Formula 3 or 4 below:

[Chemical Formula 3]

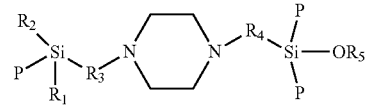

in Chemical Formula 3, $R_1$ and $R_2$, which are identical to or different from each other, are each a C1-C10 alkyl group, $R_3$ and $R_4$, which are identical to or different from each other, are each a C1-C10 alkylene group, $R_5$ is a C1-C10 alkyl group, and P is a conjugated diene-based polymer chain; and

[Chemical Formula 4]

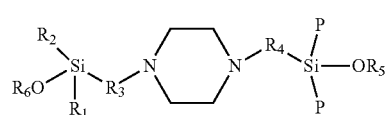

in Chemical Formula 4, $R_1$ and $R_2$, which are identical to or different from each other, are each a C1-C10 alkyl group, $R_3$ and $R_4$, which are identical to or different from each other, are each a C1-C10 alkylene group, and $R_5$ and $R_6$, which are identical to or different from each other, are each a C1-C10 alkyl group.

The modified conjugated diene-based polymer represented by Chemical Formula 3 is configured such that three portions are coupled, and the modified conjugated diene-based polymer represented by Chemical Formula 4 is configured such that two portions are coupled. Particularly, a structure in which both sides of a central piperazine are asymmetric may be formed, and the structures of the conjugated diene-based polymer chains coupled with the modifier may be identical to or different from each other.

The conjugated diene monomer and the vinyl aromatic monomer are described as above.

The solvent is not particularly limited, so long as it may be applied in the polymerization or copolymerization of the conjugated diene monomer, and may be exemplified by a hydrocarbon, or may include at least one selected from the group consisting of n-pentane, n-hexane, n-heptane, isooctane, cyclohexane, toluene, benzene, and xylene.

The organo-alkali metal compound may include at least one selected from the group consisting of an organolithium compound, an organosodium compound, an organopotassium compound, an organorubidium compound, and an organocesium compound.

For example, the organometallic compound may include at least one selected from the group consisting of methyllithium, ethyllithium, isopropyllithium, n-butyllithium, sec-butyllithium, tert-butyllithium, n-decyllithium, tert-octyllithium, phenyllithium, 1-naphthyllithium, n-eicosyllithium, 4-butylphenyllithium, 4-tolyllithium, cyclohexyllithium, 3,5-di-n-heptylcyclohexyllithium, and 4-cyclopentyllithium. Preferable as the organo-alkali metal compound is n-butyllithium, sec-butyllithium or a mixture thereof.

Alternatively, the organo-alkali metal compound may include at least one selected from the group consisting of naphthyl sodium, naphthyl potassium, lithium alkoxide, sodium alkoxide, potassium alkoxide, lithium sulfonate, sodium sulfonate, potassium sulfonate, lithium amide, sodium amide, and potassium amide, and may be used in combination with another organometallic compound.

In an embodiment of the present invention, the organo-alkali metal compound may be used in an amount of 0.01 to 10 mmol, 0.05 to 5 mmol, 0.1 to 2 mmol, or 0.1 to 1 mmol, based on 100 g in total of the monomer. When the amount of the organometallic compound falls in the above range, a conjugated diene-based polymer optimal for use in the preparation of a modified conjugated diene-based polymer may be obtained.

The hydrocarbon solvent may be exemplified by a hydrocarbon, or may include at least one selected from the group consisting of n-pentane, n-hexane, n-heptane, isooctane, cyclohexane, toluene, benzene, and xylene, but the present invention is not necessarily limited thereto.

In a), the polymerization may be exemplified by anionic polymerization

Specifically, the polymerization in a) may be living anionic polymerization, in which an active end is obtained through a growth reaction involving anions.

Also, the polymerization in a) may be either high-temperature polymerization or room-temperature polymerization.

High-temperature polymerization is a polymerization process that comprises adding the organometallic compound and then applying heat to increase the reaction temperature, and room-temperature polymerization is a polymerization process that takes place in such a way that heat is not applied after the organometallic compound is added.

The polymerization in a) may take place at a temperature ranging from −20 to 200° C., preferably 0 to 150° C., and more preferably 10 to 120° C.

As used herein, the active conjugated diene-based polymer having an alkali metal end refers to a polymer comprising a polymer anion and an alkali metal cation, which are coupled with each other.

In the method of preparing the modified conjugated diene-based polymer according to the present invention, the polymerization in (a) may be performed with the additional use of a polar additive.

The polar additive may be a base, or may include ether, amine or mixtures thereof. Specifically, it may be selected from the group consisting of tetrahydrofuran, ditetrahydrofurylpropane, diethylether, cycloamylether, dipropylether, ethylenedimethylether, ethylenedimethylether, diethyleneglycol, dimethylether, tert-butoxyethoxyethane bis(2-dimethylaminoethyl)ether, (dimethylaminoethyl)ethylether, trimethylamine, triethylamine, tripropylamine, and tetramethylethylethylenediamine, and is preferably tetrahydrofuran, ditetrahydropropylpropane, triethylamine, or tetramethylethylenediamine.

The polar additive may be used in an amount of 0.001 to 50 g, preferably 0.001 to 10 g, and more preferably 0.005 to 1 g, based on 100 g in total of the added monomer.

The polar additive may be used in an amount of 0.001 to 10 g, preferably 0.005 to 1 g, and more preferably 0.005 to 0.1 g, based on 1 mmol in total of the added organo-alkali metal compound.

When the conjugated diene monomer and the aromatic vinyl monomer are copolymerized, a block copolymer may be easily prepared due to the difference in the reaction rates therebetween. However, when the polar additive is added, the low reaction rate of the vinyl aromatic compound may be increased to thus obtain the microstructure of the corresponding copolymer, for example, a random copolymer.

In b), the active polymer having the alkali metal end obtained in a) may be coupled or reacted with the compound represented by Chemical Formula 1 below, yielding the modified conjugated diene-based polymer represented by Chemical Formula 2:

[Chemical Formula 1]

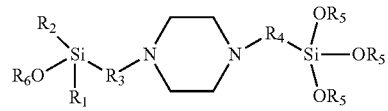

in Chemical Formula 1, $R_1$ and $R_2$, which are identical to or different from each other, are each a C1-C10 alkyl group, $R_3$ and $R_4$, which are identical to or different from each other, are each a C1-C10 alkylene group, and $R_5$ and $R_6$, which are identical to or different from each other, are each a C1-C10 alkyl group.

The compound represented by Chemical Formula 1 is a modifier, and may form an asymmetric structure or may form a structure in which coupling is carried out at both sides of a central piperazine. When the alkoxy groups are asymmetrically provided in this way, the coupling position may be controlled using the difference in reactivity of individual alkoxy groups. Thereby, when the rubber polymer is mixed with silica, a site that is able to react with silica may be reliably provided, while the steric effect between the polymer and the silica may be minimized.

In b), the molar equivalent ratio of the compound represented by Chemical Formula 1 and the active conjugated diene-based polymer preferably falls in the range of 1:0.1 to 1:100, and more preferably 1:0.1 to 1:10.

The compound represented by Chemical Formula 1 may be used in an amount of 0.01 to 10 mol, preferably 0.05 to 5 mol, and more preferably 0.1 to 1 mol based on 1 mol of the active conjugated diene-based polymer. Given the above content range, the coupling reaction of the conjugated diene-based polymer is asymmetrically induced using the difference in reactivity due to the asymmetry of silyl alkoxy groups, thereby minimizing the steric effect to thus maximize the affinity for silica.

In b), the alkali metal end of the active conjugated diene-based polymer is modified with the compound represented by Chemical Formula 1.

Also, b) is performed at 0 to 90° C. for 1 min to 5 hr.

The compound represented by Chemical Formula 1 is added to the active polymer, thereby increasing vulcanization rate and wear resistance and realizing desired rolling resistance.

The method of preparing the modified conjugated diene-based polymer according to an embodiment of the present invention may be performed in a batch manner, or alternatively in a continuous manner using at least one reactor.

The modified conjugated diene-based polymer is the compound represented by Chemical Formula 2 below:

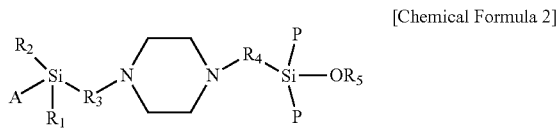

[Chemical Formula 2]

in Chemical Formula 2, $R_1$ and $R_2$, which are identical to or different from each other, are each a C1-C10 alkyl group, $R_3$ and $R_4$, which are identical to or different from each other, are each a C1-C10 alkylene group, $R_5$ is a C1-C10 alkyl group, and A is P or $OR_6$, wherein P is a conjugated diene-based polymer chain and $R_6$ is a C1-C10 alkyl group.

This polymer preferably has a structure in which three $OR_5$ groups linked with Si connected to $R_4$ in Chemical Formula 1 are substituted with conjugated diene-based polymer chains through the reaction, or one or two of the three $OR_5$ groups are substituted with a conjugated diene-based polymer chain(s) through the reaction.

The modified conjugated diene-based polymer may exhibit viscoelastic properties. When measured at 10 Hz using DMA after mixing with silica, Tan δ at 0° C. may be in the range of 0.4 to 1, or 0.5 to 1. Given the above Tan δ range, desired skid resistance or wet resistance may be obtained.

Also, Tan δ at 60° C. may be in the range of 0.3 to 0.2, or 0.15 to 0.1. Given the above Tan δ range, desired rolling resistance or rotational resistance (RR) may be obtained.

The modified conjugated diene-based polymer may be a chain composed of a conjugated diene monomer alone or both a conjugated diene monomer and an aromatic vinyl monomer.

Still another aspect of the present invention addresses a modified conjugated diene-based polymer rubber composition comprising 100 parts by weight of the modified conjugated diene-based polymer and 0.1 to 200 parts by weight of an inorganic filler.

The amount of the inorganic filler may be 10 to 150 parts by weight, or 50 to 100 parts by weight.

The inorganic filler may include at least one selected from the group consisting of silica, carbon black, and a mixture thereof. When the inorganic filler is silica, dispersibility is significantly increased and the end of the modified conjugated diene-based polymer of the invention may be coupled with silica particles, thus significantly decreasing hysteresis loss.

The modified conjugated diene-based polymer rubber composition may further comprise a silane coupling agent.

The modified conjugated diene-based polymer rubber composition may further comprise an additional conjugated diene-based polymer.

The additional conjugated diene-based polymer may include SBR (styrene-butadiene rubber), BR (butadiene rubber), natural rubber, or mixtures thereof. SBR may be exemplified by SSBR (solution styrene-butadiene rubber).

When the additional conjugated diene-based polymer is further added, the modified conjugated diene-based polymer rubber composition may comprise 20 to 100 parts by weight of the modified conjugated diene-based polymer and 0 to 80 parts by weight of the additional conjugated diene-based polymer.

Alternatively, the modified conjugated diene-based polymer rubber composition according to the present invention may comprise 20 to 99 parts by weight of the modified conjugated diene-based polymer and 1 to 80 parts by weight of the additional conjugated diene-based polymer.

Alternatively, the modified conjugated diene-based polymer rubber composition according to the present invention may comprise 10 to 100 parts by weight of the modified conjugated diene-based polymer, 0 to 90 parts by weight of the additional conjugated diene-based polymer, 0 to 100 parts by weight of carbon black, 5 to 200 parts by weight of silica, and 2 to 20 parts by weight of a silane coupling agent.

Alternatively, the modified conjugated diene-based polymer rubber composition according to the present invention may comprise 10 to 100 parts by weight of the modified conjugated diene-based polymer, 0 to 90 parts by weight of the additional conjugated diene-based polymer, 0 to 100 parts by weight of carbon black, 5 to 200 parts by weight of silica, and 2 to 20 parts by weight of a silane coupling agent, in which the total weight of the modified conjugated diene-based polymer and the additional conjugated diene-based polymer may be 100 parts by weight.

Alternatively, the modified conjugated diene-based polymer rubber composition according to the present invention may comprise 100 parts by weight of a polymer mixture comprising 10 to 99 wt % of the modified conjugated diene-based polymer and 1 to 90 wt % of the additional conjugated diene-based polymer, 1 to 100 parts by weight of carbon black, 5 to 200 parts by weight of silica, and 2 to 20 parts by weight of a silane coupling agent.

In addition, the modified conjugated diene-based polymer rubber composition may further comprise 1 to 100 parts by weight of oil. The oil may be exemplified by mineral oil or a softener.

The oil may be used in an amount of, for example, 10 to 100 parts by weight, or 20 to 80 parts by weight, based on 100 parts by weight of the conjugated diene-based copolymer. Given the above oil content range, desired properties may be exhibited, and the rubber composition may be appropriately softened, thus increasing processability.

Yet another aspect of the present invention addresses a modifier, which is a compound represented by Chemical Formula 1 below:

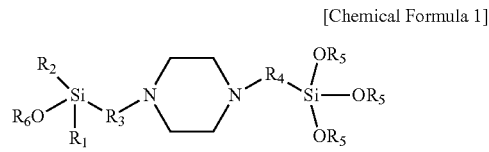

[Chemical Formula 1]

in Chemical Formula 1, $R_1$ and $R_2$, which are identical to or different from each other, are each a C1-C10 alkyl group, $R_3$ and $R_4$, which are identical to or different from each other, are each a C1-C10 alkylene group, and $R_5$ and $R_6$, which are identical to or different from each other, are each a C1-C10 alkyl group.

The modifier, which is the compound represented by Chemical Formula 1, has an asymmetric structure in which one alkoxy group is provided at one end and three alkoxy groups are provided at the other end, and thus a reaction for coupling the anions at the ends may be selectively carried out before modification.

When $R_3$ and $R_4$ are different from each other, a coupling reaction is preferentially carried out at the short branch position, and thus the modified polymer structure may be produced in a branched form, thereby increasing processability. On the other hand, when $R_3$ and $R_4$ are identical to each other, a coupling reaction is preferentially carried out at the position where the number of alkoxy groups is higher, thus forming a modified polymer having a linear structure, thereby ensuring desired rolling resistance.

Hence, the selective reaction enables the control of the polymer structure after modification and also makes it possible to control the formation of a linear or branched structure, significantly affecting the properties of tires.

Still yet another aspect of the present invention addresses a tire or tire tread using the modified conjugated diene-based polymer rubber composition described above.

The tire or tire tread is manufactured using the rubber composition comprising the modified conjugated diene-based polymer, which has high processability and superior compatibility with the inorganic filler, and thereby can manifest high tensile strength, wear resistance, and wet skid resistance, as well as low rolling resistance.

MODE FOR INVENTION

A better understanding of the present invention may be obtained via the following examples. However, the examples of the present invention may be changed in various forms, and are not construed as limiting the scope of the present invention. The examples of the present invention are provided to fully describe the present invention to those having ordinary knowledge in the art to which the present invention pertains.

Example 1

270 g of styrene, 710 g of 1,3-butadiene, 5000 g of n-hexane, and 0.86 g of 2,2-bis(2-oxolanyl)propane as a polar additive were placed in a 20 L autoclave reactor, and then the temperature inside the reactor was raised to 40° C. When the temperature inside the reactor reached 40° C., 4 mmol of n-butyllithium was placed in the reactor, followed by an adiabatic heating reaction. After about 20 min, 20 g of 1,3-butadiene was added. After 5 min, dimethylethoxy propyl silyl triethoxy methyl silyl piperazine (using the above material) was added in an amount of 0.8 equivalents based on the amount of active lithium, and the reaction was carried out for 15 min. Then, the polymerization reaction was stopped using ethanol, and 45 mL of a solution of 0.3 wt % BHT (butylated hydroxytoluene) antioxidant in hexane was added.

The resulting polymer was placed in water warmed with steam and stirred to remove the solvent, followed by roll drying to remove the remaining solvent and water, yielding a modified conjugated diene-based polymer. The results of analysis of the modified conjugated diene-based polymer thus obtained are shown in Table 1 below.

Example 2

270 g of styrene, 710 g of 1,3-butadiene, 5000 g of n-hexane, and 0.86 g of 2,2-bis(2-oxolanyl)propane as a polar additive were placed in a 20 L autoclave reactor, and then the temperature inside the reactor was raised to 40° C. When the temperature inside the reactor reached 40° C., 4 mmol of n-butyllithium was placed in the reactor, followed by an adiabatic heating reaction. After about 20 min, 20 g of 1,3-butadiene was added. After 5 min, dimethylethoxy propyl silyl triethoxy methyl silyl piperazine (using the above material) was added in an amount of 1.0 equivalent based on the amount of active lithium, and the reaction was carried out for 15 min. Then, the polymerization reaction was stopped using ethanol, and 45 mL of a solution of 0.3 wt % BHT (butylated hydroxytoluene) antioxidant in hexane was added.

The resulting polymer was placed in water warmed with steam and stirred to remove the solvent, followed by roll drying to remove the remaining solvent and water, yielding a modified conjugated diene-based polymer. The results of analysis of the modified conjugated diene-based polymer thus obtained are shown in Table 1 below.

Comparative Example 1

270 g of styrene, 710 g of 1,3-butadiene, 5000 g of n-hexane, and 0.86 g of 2,2-bis(2-oxolanyl)propane as a polar additive were placed in a 20 L autoclave reactor, and then the temperature inside the reactor was raised to 40° C. When the temperature inside the reactor reached 40° C., 4 mmol of n-butyllithium was placed in the reactor, followed by an adiabatic heating reaction. After about 20 min, 20 g of 1,3-butadiene was added. After 5 min, N,N-bis(triethoxysilylpropyl)aminopropyl-1-imidazole was added in an amount of 0.5 equivalents based on the amount of active lithium, and the reaction was carried out for 15 min. Then, the polymerization reaction was stopped using ethanol, and 45 mL of a solution of 0.3 wt % BHT (butylated hydroxytoluene) antioxidant in hexane was added.

The resulting polymer was placed in water warmed with steam and stirred to remove the solvent, followed by roll drying to remove the remaining solvent and water, yielding a modified conjugated diene-based polymer. The results of analysis of the modified conjugated diene-based polymer thus obtained are shown in Table 1 below.

Comparative Example 2

A modified conjugated diene-based polymer was prepared in the same manner as in Comparative Example 1, with the exception that N,N-bis(triethoxysilylpropyl)aminopropyl-1-imidazole was added in an amount of 1.0 equivalent based on the amount of active lithium. The results of analysis of the modified conjugated diene-based polymer thus obtained are shown in Table 1 below.

Comparative Example 3

A modified conjugated diene-based polymer was prepared in the same manner as in Example 1, with the exception that the modifier was not added. The results of analysis of the modified conjugated diene-based polymer thus obtained are shown in Table 1 below.

TABLE 1

|  |  | Ex. 1 | Ex. 2 | C. Ex. 1 | C. Ex. 2 | C. Ex. 3 |
|---|---|---|---|---|---|---|
| Sample |  | A | B | C | D | E |
| Modifier | Kind | dimethylethoxy propyl silyl triethoxy methyl silyl piperazine | | N,N-bis(triethoxysilylpropyl)amino propyl-1-imidazole | | — |
|  | Amount (mol eq) | 0.8 | 1.0 | 0.5 | 1.0 | — |
| Mooney |  | 68 | 66 | 74 | 76 | 66 |
| Styrene (%) |  | 26 | 26 | 26 | 26 | 26 |
| Vinyl (%) |  | 43 | 43 | 43 | 43 | 40 |
| GPC ($\times 10^4$) | Mn | 32 | 32 | 31 | 31 | 33 |

TABLE 1-continued

|  | Ex. 1 | Ex. 2 | C. Ex. 1 | C. Ex. 2 | C. Ex. 3 |
|---|---|---|---|---|---|
| Mw | 58 | 58 | 54 | 54 | 50 |
| PDI | 1.8 | 1.7 | 1.8 | 1.8 | 1.5 |

The conjugated diene-based polymer rubber compositions were prepared using, as raw rubber, samples A to E, shown in Table 1, under the mixing conditions of Table 2 below. The unit of material in Table 2 is phr, based on 100 parts by weight of rubber.

Specifically, the conjugated diene-based polymer rubber composition was kneaded through primary kneading and secondary kneading. Upon primary kneading, raw rubber (conjugated diene-based polymer), a filler, an organosilane coupling agent, oil, zinc oxide, a stearic acid antioxidant, an anti-aging agent, wax and an accelerator were kneaded using a Banbury mixer provided with a temperature controller. For this, the temperature of the kneader was controlled, and a first mixture was obtained at a discharge temperature of 145 to 155° C. Upon secondary kneading, the first mixture was cooled to room temperature, after which rubber, sulfur and a vulcanization accelerator were placed in the kneader, followed by mixing at 100° C. or less, thus obtaining a second mixture. Finally, curing was performed at 100° C. for 20 min, yielding the conjugated diene-based polymer rubber compositions of Preparation Examples 1 and 2 using, as raw rubber, the polymers of Examples 1 and 2, and of Comparative Preparation Examples 1 to 3 using the polymers of Comparative Examples 1 to 3 as raw rubber.

TABLE 2

|  | Material | Amount (unit: phr) |
|---|---|---|
| Primary kneading | Rubber | 137.5 |
|  | Silica | 70.0 |
|  | Coupling agent | 11.2 |
|  | Oil | — |
|  | Zinc oxide | 3.0 |
|  | Stearic acid | 2.0 |
|  | Antioxidant | 2.0 |
|  | Anti-aging agent | 2.0 |
|  | Wax | 1.0 |
| Secondary kneading | Rubber accelerator | 1.75 |
|  | Sulfur | 1.5 |
|  | Vulcanization accelerator | 2.0 |
|  | Total weight | 234.0 |

The properties of the prepared rubber compositions were measured through the following methods.

1) Tensile Testing

According to the tensile testing method of ASTM 412, the tensile strength upon cutting a test sample and tensile stress (300% modulus) at 300% elongation were measured. For this, the tensile strength, modulus, and elongation were measured at a tensile speed of 50 cm/min at room temperature using, as a tensile tester, a Universal Test Machine 4204, made by Instron.

2) Viscoelasticity

A dynamic mechanical analyzer made by TA was used. When undergoing strain under conditions of a frequency of 10 Hz in the torsional mode and a measurement temperature (ranging from −60 to 60° C.), the Tan δ of each sample was measured. The Payne effect was represented by the difference between the minimum and the maximum in the strain sweep range of 0.28 to 40%. The lower the Payne effect, the higher the dispersibility of the filler such as silica. When Tan δ at 0° C., which is a low temperature, was increased, wet skid resistance became superior, and when Tan δ at 60° C., which is a high temperature, was decreased, hysteresis loss was reduced, resulting in low rolling resistance of tires and thus superior fuel economy. Table 3 below shows the properties of the vulcanized rubber.

TABLE 3

| Sample | Prep. Ex. 1 A | Prep. Ex. 2 B | C. Prep. Ex. 1 C | C. Prep. Ex. 2 D | C. Prep. Ex. 3 E |
|---|---|---|---|---|---|
| 300% Modulus (Kgf/cm$^2$) | 143 | 142 | 144 | 144 | 102 |
| Tensile strength (Kgf/cm$^2$) | 146 | 156 | 147 | 146 | 105 |
| Tanδ at 0° C. | 112 | 114 | 113 | 117 | 81 |
| Tanδ at 60° C. | 106 | 100 | 101 | 99 | 82 |

As is apparent from the results of Table 3, compared to Comparative Preparation Example 3, the modified conjugated diene-based polymer rubber compositions of Preparation Examples 1 and 2 according to the present invention were significantly increased in 300% modulus (tensile stress), tensile strength and Tan δ values at 0° C. and 60° C. Also, the conjugated diene-based polymer rubber compositions of Preparation Examples 1 and 2 according to the present invention exhibited 300% modulus (tensile stress) and tensile strength equal to those of Comparative Preparation Examples 1 and 2, and furthermore, manifested low rolling resistance based on Tan δ at 60° C. Therefore, when the modified conjugated diene-based polymer rubber composition of the invention was used for a tire, rolling resistance was decreased and thus superior fuel economy resulted.

The invention claimed is:

1. A modified conjugated diene-based polymer represented by Chemical Formula 2 below:

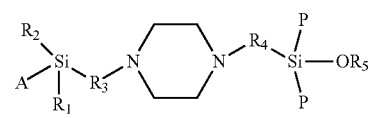

[Chemical Formula 2]

in Chemical Formula 2, $R_1$ and $R_2$, which are identical to or different from each other, are each a C1-C10 alkyl group, $R_3$ and $R_4$, which are identical to or different from each other, are each a C1-C10 alkylene group, $R_5$ is a C1-C10 alkyl group, and A is P or $OR_6$, wherein P is a conjugated diene-based polymer chain and $R_6$ is a C1-C10 alkyl group.

2. The modified conjugated diene-based polymer of claim 1, wherein the Chemical Formula 2 is Chemical Formula 3 below:

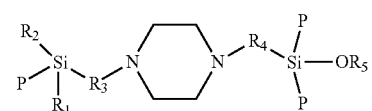

[Chemical Formula 3]

in Chemical Formula 3, $R_1$ and $R_2$, which are identical to or different from each other, are each a C1-C10 alkyl group, $R_3$ and $R_4$, which are identical to or different from each other, are each a C1-C10 alkylene group, $R_5$ is a C1-C10 alkyl group, and P is a conjugated diene-based polymer chain.

3. The modified conjugated diene-based polymer of claim 1, wherein the Chemical Formula 2 is Chemical Formula 4 below:

[Chemical Formula 4]

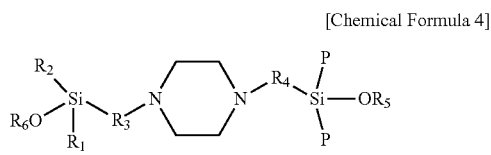

in Chemical Formula 4, $R_1$ and $R_2$, which are identical to or different from each other, are each a C1-C10 alkyl group, $R_3$ and $R_4$, which are identical to or different from each other, are each a C1-C10 alkylene group, and $R_5$ and $R_6$, which are identical to or different from each other, are each a C1-C10 alkyl group.

4. The modified conjugated diene-based polymer of claim 1, wherein the modified conjugated diene-based polymer has a number average molecular weight (Mn) of 1,000 to 2,000,000 g/mol.

5. The modified conjugated diene-based polymer of claim 1, wherein the modified conjugated diene-based polymer has a polydispersity index (Mw/Mn) of 1 to 10.

6. The modified conjugated diene-based polymer of claim 1, wherein the modified conjugated diene-based polymer has a vinyl content of 10 wt % or more.

7. The modified conjugated diene-based polymer of claim 1, wherein the conjugated diene-based polymer chain is derived from a homopolymer of a conjugated diene monomer or a copolymer of a conjugated diene monomer and a vinyl aromatic monomer.

8. The modified conjugated diene-based polymer of claim 1, wherein the modified conjugated diene-based polymer comprises 0.0001 to 50 wt % of an aromatic vinyl monomer based on 100 wt % in total of a conjugated diene monomer and the aromatic vinyl monomer.

9. The modified conjugated diene-based polymer of claim 1, wherein the modified conjugated diene-based polymer has a Mooney viscosity of 40 or more.

10. A method of preparing a modified conjugated diene-based polymer, comprising:
    a) polymerizing a conjugated diene monomer, or a conjugated diene monomer and an aromatic vinyl monomer, using a hydrocarbon solvent in presence of an organo-alkali metal compound, thus forming an active conjugated diene-based polymer having an alkali metal end; and
    b) coupling or reacting the active conjugated diene-based polymer having the alkali metal end with a compound represented by Chemical Formula 1 below, yielding a modified conjugated diene-based polymer represented by Chemical Formula 2 below:

[Chemical Formula 1]

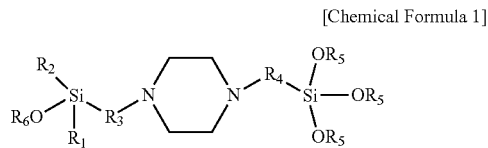

in Chemical Formula 1, $R_1$ and $R_2$, which are identical to or different from each other, are each a C1-C10 alkyl group, $R_3$ and $R_4$, which are identical to or different from each other, are each a C1-C10 alkylene group, and $R_5$ and $R_6$, which are identical to or different from each other, are each a C1-C10 alkyl group; and

[Chemical Formula 2]

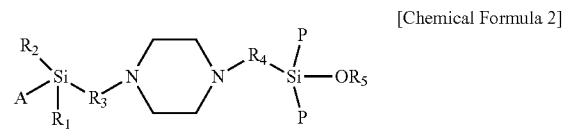

in Chemical Formula 2, $R_1$ and $R_2$, which are identical to or different from each other, are each a C1-C10 alkyl group, $R_3$ and $R_4$, which are identical to or different from each other, are each a C1-C10 alkylene group, $R_5$ is a C1-C10 alkyl group, and A is P or $OR_6$, wherein P is a conjugated diene-based polymer chain and $R_6$ is a C1-C10 alkyl group.

11. The method of claim 10, wherein the organo-alkali metal compound is used in an amount of 0.01 to 10 mmol based on 100 g in total of the monomer.

12. The method of claim 10, wherein in b), a molar equivalent ratio of the compound represented by Chemical Formula 1 and the active conjugated diene-based polymer is 1:0.1 to 1:100.

13. The method of claim 10, wherein in b), a molar equivalent ratio of the compound represented by Chemical Formula 1 and the active conjugated diene-based polymer is 1:0.1 to 1:10.

14. The method of claim 10, wherein the polymerizing in a) is performed with additional use of a polar additive.

15. The method of claim 14, wherein the polar additive is added in an amount of 0.001 to 10 g based on 1 mmol in total of the organo-alkali metal compound.

16. A modified conjugated diene-based polymer rubber composition comprising 100 parts by weight of the modified conjugated diene-based polymer of claim 1 and 0.1 to 200 parts by weight of an inorganic filler.

17. The modified conjugated diene-based polymer rubber composition of claim 16, wherein the inorganic filler comprises at least one selected from the group consisting of silica, carbon black, and a mixture thereof.

18. A modifier, which is a compound represented by Chemical Formula 1 below:

[Chemical Formula 1]

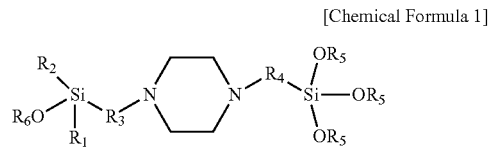

in Chemical Formula 1, $R_1$ and $R_2$, which are identical to or different from each other, are each a C1-C10 alkyl group, $R_3$ and $R_4$, which are identical to or different from each other, are each a C1-C10 alkylene group, and $R_5$ and $R_6$, which are identical to or different from each other, are each a C1-C10 alkyl group.

19. A tire or tire tread comprising the modified conjugated diene-based polymer rubber composition of claim 16.

* * * * *